(12) United States Patent
Pless (10) Patent No.: US 11,453,544 B2
(45) Date of Patent: Sep. 27, 2022

(54) SHIPPING CONTAINER SYSTEMS FOR LIVE SAMPLES AND RELATED DIE CUT TRAY INSERTS

(71) Applicant: Whimsical Wings Farms, Inc., Kernersville, NC (US)

(72) Inventor: Donna Hughes Pless, Kernersville, NC (US)

(73) Assignee: Whimsical Wings Farms, Inc., Kernersville, NC (US)

(*) Notice: Subject to any disclaimer, the term of this patent is extended or adjusted under 35 U.S.C. 154(b) by 201 days.

(21) Appl. No.: 15/930,630

(22) Filed: May 13, 2020

(65) Prior Publication Data

US 2020/0361699 A1 Nov. 19, 2020

Related U.S. Application Data

(60) Provisional application No. 62/848,103, filed on May 15, 2019.

(51) Int. Cl.
*B65D 85/52* (2006.01)
*B65D 5/42* (2006.01)
*B65D 81/02* (2006.01)

(52) U.S. Cl.
CPC .......... *B65D 85/52* (2013.01); *B65D 5/4295* (2013.01); *B65D 81/025* (2013.01); *B65D 2205/02* (2013.01); *B65D 2581/053* (2013.01)

(58) Field of Classification Search
CPC .......... A01G 9/02; B65D 5/42; B65D 5/4295; B65D 81/02; B65D 81/025; B65D 85/52; B65D 2205/02; B65D 2581/053

USPC ............................................... 47/84; 206/423
See application file for complete search history.

(56) References Cited

U.S. PATENT DOCUMENTS

| 2,403,840 | A |   | 7/1946  | Ashurst  |                  |
|-----------|---|---|---------|----------|------------------|
| 3,342,329 | A | * | 9/1967  | Knight   | B65D 85/52       |
|           |   |   |         |          | 229/198          |
| 4,170,301 | A | * | 10/1979 | Jones    | B65D 85/52       |
|           |   |   |         |          | 47/84            |
| 4,330,059 | A | * | 5/1982  | Freeman  | B65D 5/5007      |
|           |   |   |         |          | 206/423          |
| 4,936,046 | A |   | 6/1990  | Miller   |                  |
| 4,941,572 | A | * | 7/1990  | Harris   | B65D 85/505      |
|           |   |   |         |          | 53/472           |

(Continued)

FOREIGN PATENT DOCUMENTS

CN        204137592 U   *   2/2015

*Primary Examiner* — Bryon P Gehman
(74) *Attorney, Agent, or Firm* — Stanek Lemon Crouse & Meeks, PA (57) ABSTRACT

A die cut tray insert is provided including a first face and a second face, opposite and parallel to the first face; first and second assemblies secured at one end to one of the first and second faces and configured to swing between an open position and a closed position such that a pot associated with a live sample is secured on two sides; and a third face and a fourth face, perpendicular to the first and second faces and opposite and parallel to one another, the third face configured to cover a top portion of the pot associated with the live sample and the fourth face configured to contain the pot within the first, second and third faces. The third face covering the top portion of the pot is configured to reduce spillage from the pot when the first and second assemblies are in a closed position.

18 Claims, 5 Drawing Sheets

(56) References Cited

U.S. PATENT DOCUMENTS

| | | | | |
|---|---|---|---|---|
| 5,029,708 A | * | 7/1991 | Alonso | B65D 85/52 47/84 |
| 5,038,930 A | * | 8/1991 | Holtkamp, Jr. | B65D 5/5007 229/115 |
| 5,379,549 A | | 1/1995 | Carcich et al. | |
| 5,710,641 A | * | 1/1998 | Lowry | B65D 85/505 358/479 |
| 6,446,805 B1 | * | 9/2002 | Mann | B65D 5/46112 206/423 |
| 6,814,279 B2 | | 11/2004 | Jochens | |
| 2006/0196427 A1 | | 9/2006 | Lepori | |

* cited by examiner

FIG. 1A

PARTITION
44 ECT C-FLUTE
NEED 4

FIG. 2A

PARTITION SET
44 ECT C-FLUTE

SHIPPING CONTAINER SYSTEMS FOR LIVE SAMPLES AND RELATED DIE CUT TRAY INSERTS

CLAIM OF PRIORITY

The present application claims priority to U.S. Provisional Patent Application Ser. No. 62/848,103, filed May 15, 2019, entitled *Shipping Containers for Live Samples and Related Systems and Methods*, the disclosure of which is hereby incorporated herein by reference as if set forth in its entirety.

FIELD

The present inventive concept relates generally to shipping containers and, more particularly, to containers, systems and methods for shipment and delivery of live samples.

BACKGROUND

Over the past few years, the industry of rearing and sale of live insects, such as butterflies, has increased in popularity. The sale of live butterflies, also known as butterfly farming, has focused on the sale of live adult butterflies for release at special events, such as weddings, or eggs and/or butterfly larvae included in a rearing kit for the hobbyist, or for conservation, education and/or research. Butterfly eggs and/or caterpillars have generally been sold and shipped on a potted plant, such as a milkweed plant, or on fresh cut leaves.

However, there are numerous limitations and shortcomings with present conventional containers and methods for shipping live samples, such as butterflies, butterfly caterpillars, and/or butterfly eggs. Accordingly, there is a need for improved containers and methods for safely shipping live plants.

SUMMARY

Some embodiments of the present inventive concept provide a die cut tray insert for securing live samples during shipping including a first face and a second face, opposite and parallel to the first face; first and second assemblies secured at one end to one of the first and second faces and configured to swing between an open position and a closed position such that a pot associated with the live sample is secured on two sides when the first and second assemblies are in a closed position; and a third face and a fourth face, perpendicular to the first and second faces and opposite and parallel to one another, the third face configured to cover a top portion of the pot associated with the live sample and the fourth face configured to contain the pot within the first, second and third faces. The third face covering the top portion of the pot is configured to reduce spillage from the pot when the first and second assemblies are in a closed position.

In further embodiments, the first and second assemblies may be configured to prevent the pot and live sample positioned therein from moving and/or tipping over when the die cut tray insert is positioned in a receptacle for shipping.

In still further embodiments, the first and second assemblies may each include a hemispherical margin portion on a top surface the assembly; and an angled margin portion on an inner side surface of the assembly configured to conformally surround a portion of the periphery of the pot and secure the pot within the die cut tray insert when the assembly is in the closed position.

In some embodiments, the hemispherical margin portions may include a plurality of radial slits extending from the hemispherical margin portions to provide flexible fingers in the top surface of each of the first and second assemblies.

In further embodiments, the third surface of the die cut tray insert may include a notch or slot such that a main stalk of the live sample in the pot may slide through the notch or slot when the pot is positioned in the die cut tray insert.

In still further embodiments, the tray may further include a finger hole large enough to stick at least one finger through at the center of an intersection of the first or second face and the third face of the die cut tray insert to facilitate slidably removing the die cut tray insert including the live samples in the pot.

In some embodiments, the die cut tray insert may include a corrugated type fiberboard or paperboard material.

Further embodiments of the present inventive concept may provide a container system for shipment and delivery of live samples, the system including a receptacle; a partition set; and a die cut tray insert configured to receive a pot including a live sample, the die cut tray insert including the sample configured to be surrounded by the partition set and positioned within the receptacle for shipping.

In still further embodiments, the system may further include an optional gift box positioned in the receptacle.

DETAILED DESCRIPTION

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

As discussed above, there are numerous limitations and shortcomings with present conventional containers and methods for shipping live samples, such as butterflies, butterfly caterpillars, and/or butterfly eggs. For example, there is need for shipping containers that can ship butterfly eggs, on a live plant, such as a potted plant, without causing damage to the potted plant and harm to the butterfly eggs, so that the recipient, upon receiving the potted plant and butterfly eggs, will be able to raise the butterfly eggs through the growth cycle from egg to adult butterfly and the ultimate release of the adult. Some embodiments of the present inventive concept provide containers, systems and methods for safely shipping live samples as will be discussed further below with respect to FIGS. 1A through 4.

Figure 1A:
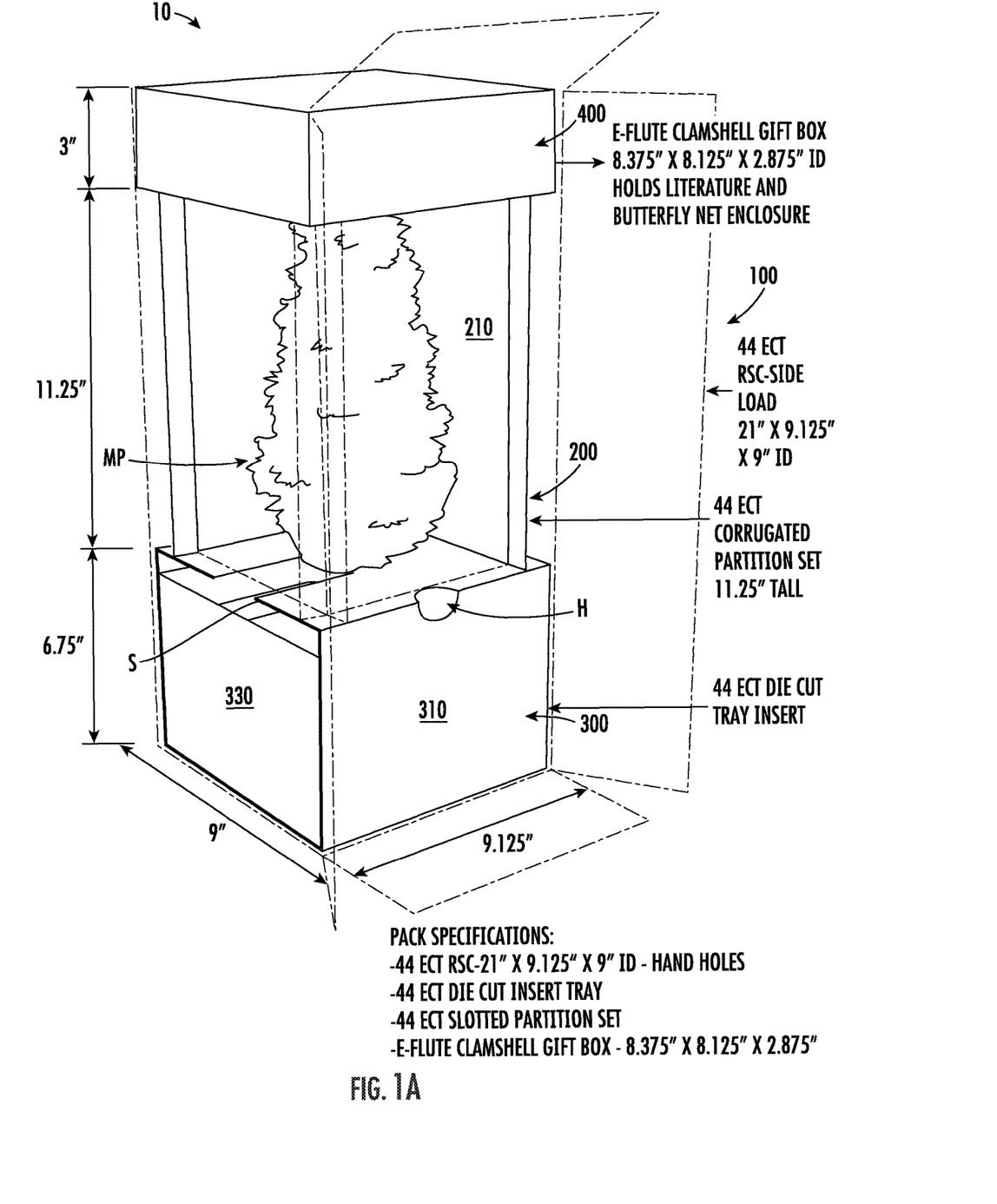
FIGS. 1A and 1B are diagrams illustrating a shipping container system for live samples according to some embodiments of the present inventive concept.
Figure 1B:
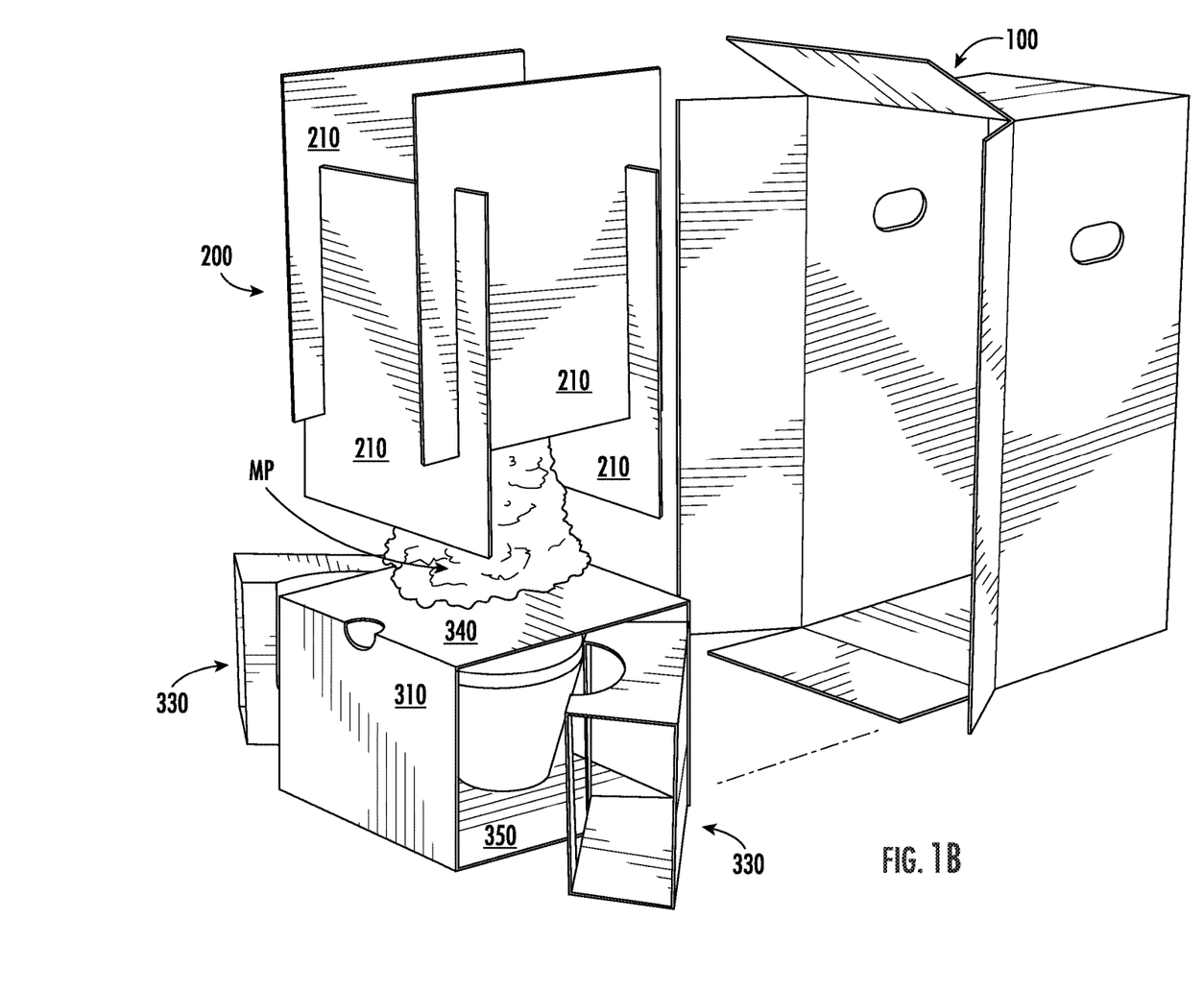

Referring first to FIGS. 1A and 1B, a container system 10 in accordance with some embodiments of the present inventive concept will be discussed. As illustrated in FIGS. 1A and 1B, the container system 10 includes a receptacle 100, a partition set 200, a die cut tray insert 300 and an optional gift box 400. The container system 10 may be used for shipment and delivery of live samples in accordance with embodiments discussed herein.

It will be understood that although embodiments of the present inventive concept discuss using the container system 10 to ship a live plant with live "eggs" thereon, embodiments of the present inventive concept are not limited thereto. The container system 10 as discussed herein may be used to ship anything that can feasibly be shipped in such a container system 10 without departing from the scope of the present inventive concept.

In some embodiments, the various elements of the container system 10, for example, the receptacle 100, the partition set 200, the die cut tray insert 300, and the optional gift box 400, may be constructed from a corrugated type fiberboard or paperboard material. However, embodiments of the present inventive concept are not limited thereto. Any suitable material may be used without departing from the scope of the present inventive concept.

Referring again to FIG. 1B, the receptacle 100 may include upper, lower, and back panels, and a front flap or flaps that may be opened and closed, forming a rectangular shaped box. The side panels may have hand holes therein for picking up the container system, and the front panel of the receptacle may be configured so that a live potted plant MP, along with at least one butterfly egg thereon, may be set in the die cut tray insert 300, the partition set 200 positioned on the die cut tray insert 300 over and surrounding leaves and stalks of the plant, and the gift box 400 positioned on the partition set 200, can be slidably side loaded into and removed from the receptacle 100. The front flap or flaps of the receptacle 100 may be sealed in the closed configuration for shipping, with, for example, packaging or shipping tape.

Although the receptacle 100, and therefore the assembled system 10, is shown as rectangular in the figures, embodiments of the present inventive concept are not limited thereto. For example, the container system may be other shaped, for example, square, without departing from the scope of the present inventive concept.

Figure 2A:
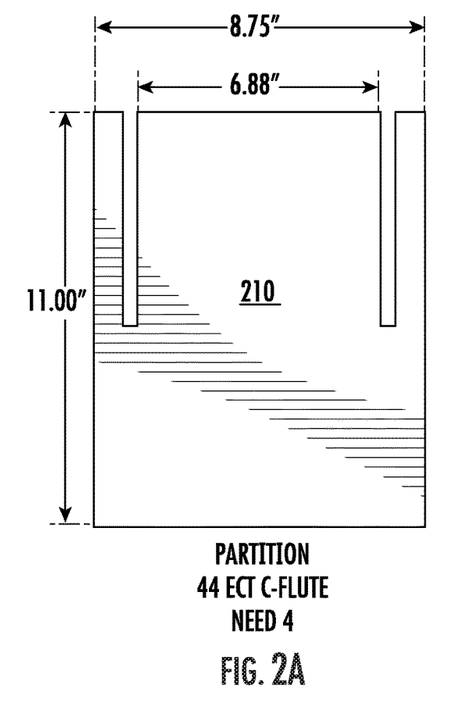
FIGS. 2A and 2B are diagrams illustrating a pattern for an individual partition and a set of four partitions assembled, respectively, for the shipping container system for live samples according to some embodiments of the present inventive concept.
Figure 2B:
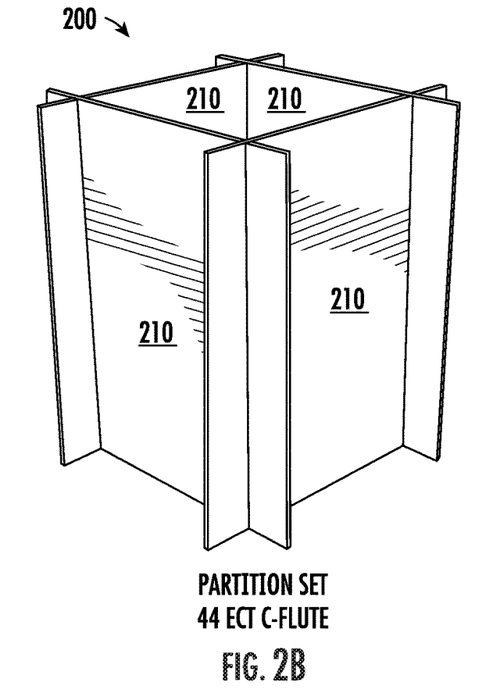

Referring to FIGS. 2A and 2B, details with respect to the partition set 200 will now be discussed. As illustrated, the partition set 200 may include individual partitions 210, each of generally rectangular shape and each including slots so that, for example, four individual partitions 210 may be assembled together to surround the leaves and stalks of the plant. Along with the receptacle 100, the partitions may protect the plant from damage and environmental elements during shipping and transport. The structure of a single partition and an assembled set of four partitions are shown in FIGS. 2A and 2B, respectively. The assembled set of partitions as shown in FIG. 2B, when positioned over the leaves and stalks of the plant for shipping may be positioned on top of the die cut tray insert 300 as shown in FIGS. 1A and 1B.

Figure 3:
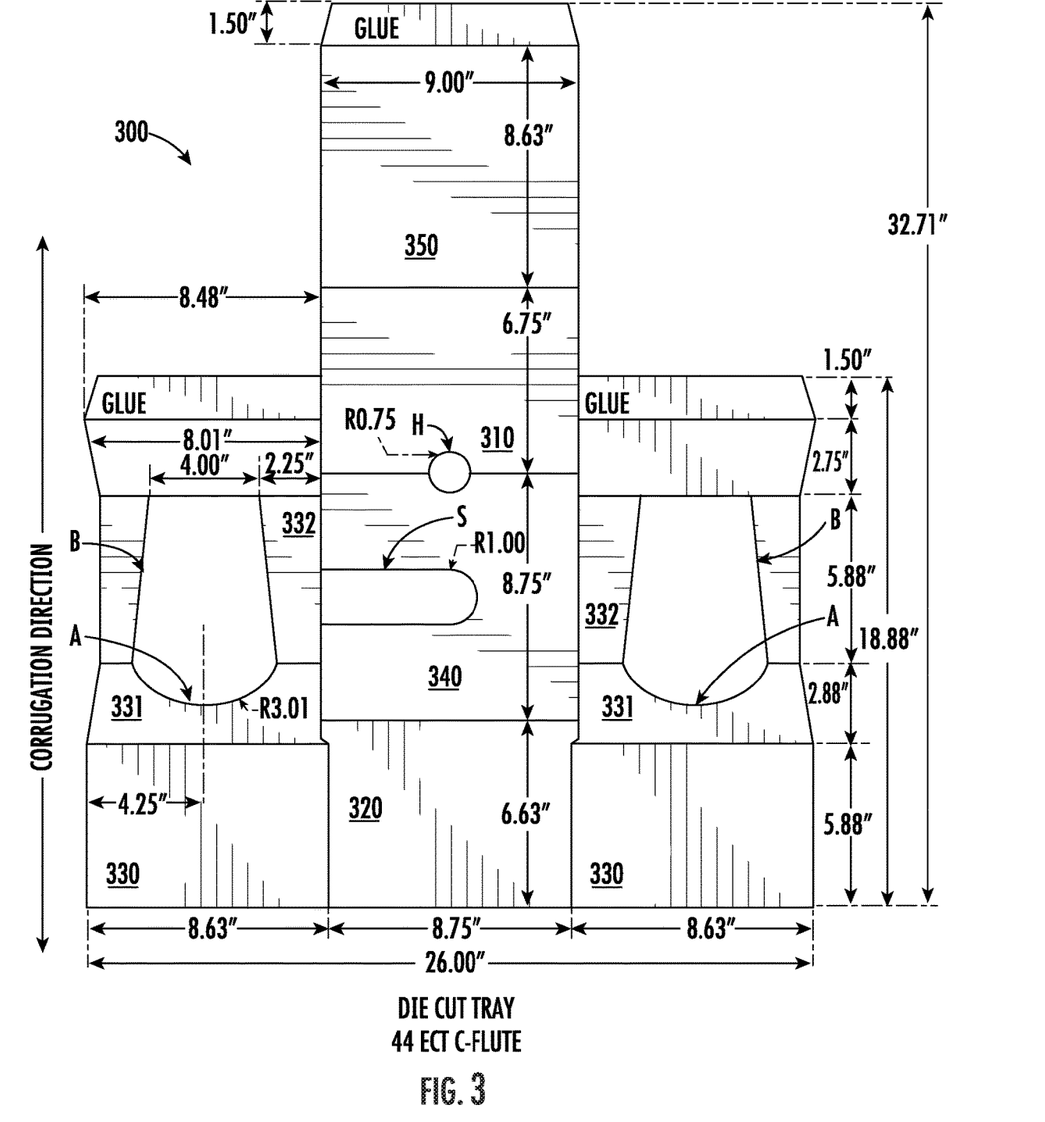
FIG. 3 is a diagram illustrating a pattern for an unassembled die cut try insert for the shipping container for live samples according to some embodiments of the present inventive concept.

Details with respect to the die cut tray insert 300 will now be discussed with respect to FIGS. 3 and 4. The die cut tray insert 300 may be configured to secure a pot including a live plant therein during shipment. FIG. 3 illustrates an example embodiment of an unassembled pattern of the die cut tray insert 300. Although the nature of the pot is not particularly limited, in some embodiments, the die cut try is configured to secure a one-gallon trade pot (6.25" depth×6.5" diameter). It will be understood that the size of the various portions of the die cut tray insert 300 may vary depending on the size of the plant to be shipped.

Figure 4:
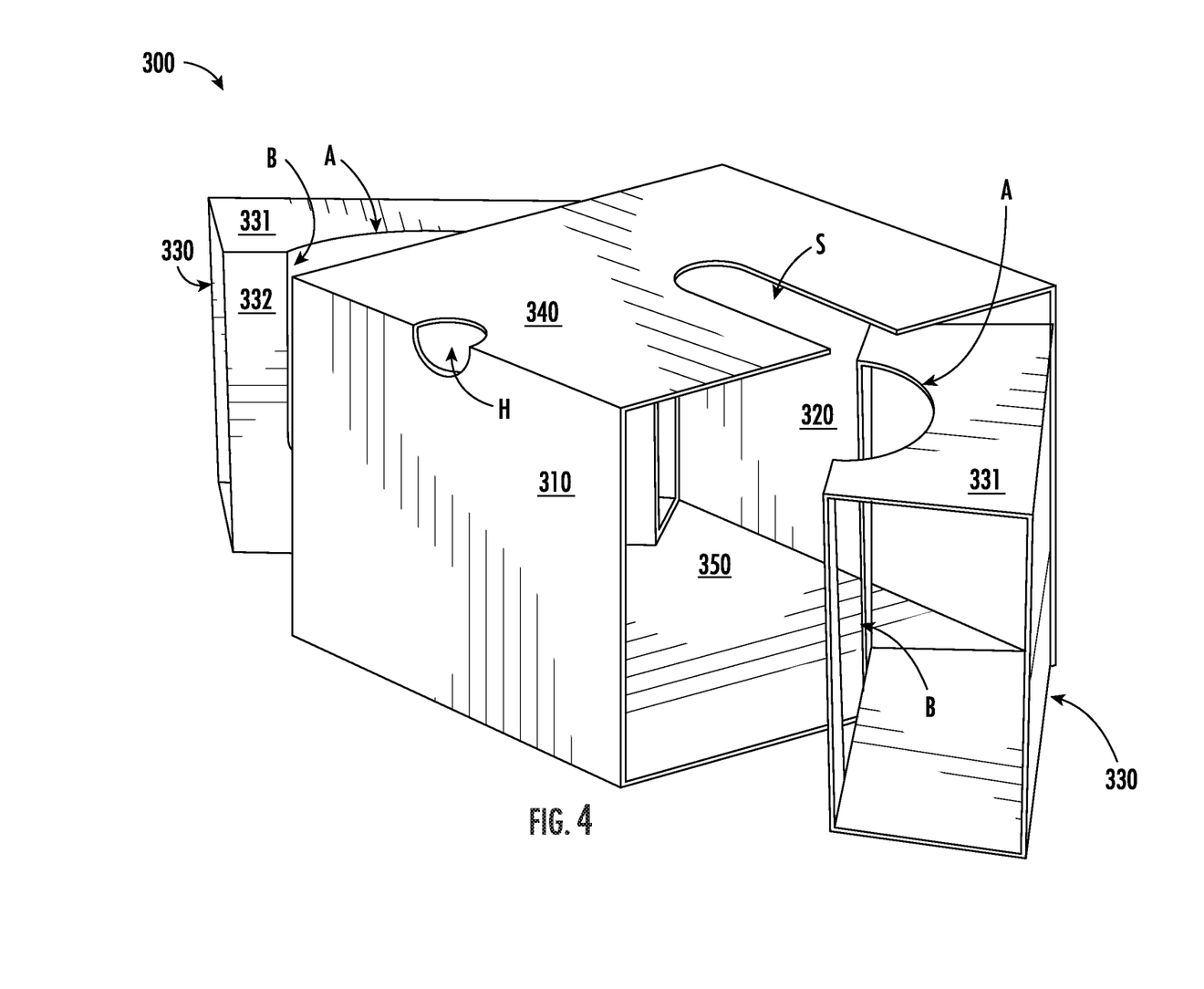
FIG. 4 is a diagram illustrating an assembled die cut tray insert for the shipping container system for live samples according to some embodiments of the present inventive concept.

As shown in FIG. 4, the assembled die cut tray insert 300 may have a front face 310; a back face 320; two side assemblies 330 configured to swing between an open position as shown in FIG. 4 and a closed position (shown in FIG. 1A) that secure the pot on two sides and reduce the likelihood that the pot and plant will move and/or tip over when the die cut tray insert 300 is positioned in the receptacle 100; a top face 340 configured to cover the top of the pot, reducing the likelihood that soil in the pot will spill during shipment; and a bottom face 350. The two side assemblies 330 may include hemispherical margin portions A on a top surface 331 of each of the side assemblies 330 and angled margin portions B on an inner side surface 332 of each of the side assemblies 330 configured to conformally surround a portion of the periphery of the pot and secure the pot within the die cut tray insert 300 when the side assemblies 330 are closed around the pot. In some embodiments, hemispherical margin portions A may optionally include a plurality radial slits (not shown) extending from the hemispherical margin portions A and provide flexible fingers in the top surface 331 of each of the side assemblies 330. The top face 340 of the assembled die cut tray may include a notch or slot S, so that the main stalk of the potted plant MP may slide through when positioning the pot and potted plant MP in the die cut tray insert 300. A finger hole H large enough to stick at least one finger through may be positioned at the center of the intersection of the front face 310 and top face 340 of the die cut tray to facilitate slidably removing the side loaded die cut tray insert 300 with potted plant MP therein, partition set 200, and optionally the gift box 400 from the receptacle 100.

Referring again to FIG. 1A, some embodiments of the present inventive concept provide a "gift box" positioned on the partitions 200. It will be understood that embodiments of the present inventive concept do not require the gift box 400 to include any "gifts." Thus, the gift box 400 and characteristics thereof are not are not particularly limited. However, in some embodiments, accessories, such as literature describing the shipped live samples, instructions for raising the live samples, such as butterflies, and/or a net enclosure to place over the plant, for example, while raising the live samples, may be provided in the gift box 400. Embodiments discussed herein include the gift box 400 disposed on top of the partition set 200 within the receptacle 100. However, embodiments of the present inventive concept are not limited thereto. For example, in some embodiments, the gift box 400 may be disposed below the die cut tray insert 300 within the receptacle 100. In some embodiments, the gift box 400 may be a clamshell box.

It will be understood that the container system 10 in accordance with embodiments discussed herein may perform a variety of functions. Thus, the container system is not limited to the transport and shipment of live samples and protection of the same from damage and the elements during transport and shipment.

To transport and/or ship live samples, the potted plant MP with, for example, butterfly eggs thereon, may be loaded into the assemble die cut tray insert 300 by sliding the pot, including the plant therein, into the die cut tray insert 300 with the main plant stalk protruding through the notch or slot S in top face 340. Side assemblies 330 may then be closed around the pot to secure the pot within the die cut tray insert 300. The partition set 200 may then be set on the die cut tray insert 300 over the leaves and main stalk of the potted plant MP, and the die cut tray insert 300, with potted plant and the partition set 200, may then be slidably side loaded into the receptacle 100. The gift box 400 and its contents (if any) may then be slidably loaded on top of the partition set 200 into the receptacle 100, and the receptacle 100 may be sealed closed for transport and/or shipping. Although this shipment method is discussed in a particular order, it will be understood that embodiments discussed herein are not limited to the order present herein. Various steps in the method may be interchanged without departing from the scope of the present inventive concept.

After delivery, the receptacle 100 may be opened and the contents, i.e., the partition set 200, disposed over the potted plant MP set in the die cut tray insert 300, may be slidably removed sideways from the receptacle 100. The finger hole may facilitate removal of the die cut tray insert 300, potted plant MP and partition set 200 thereon from the receptacle 100. The gift box 400 may be removed with the potted plant MP set in the die cut tray insert 300 and partition set 200, or optionally may be removed prior to removing the partition set 200 and the potted plant MP set in the die cut tray insert 300. The partition set 200 may be removed, and the potted plant MP may be removed from the die cut tray insert 300. A net enclosure, as may be provided as part of the contents of the gift box 400, may be placed over the potted plant MP to protect butterfly eggs that may be shipped on the potted plant MP, as well as larvae and pupae of butterflies that may develop from the butterfly eggs through the butterfly lifecycle.

As discussed above, some embodiments of the present inventive concept provide a container system that may be used for shipment and delivery of various live samples. In some embodiments, the live samples may be provided on a live plant, such as a potted live plant. In some embodiments, the plant may be a host plant on which the monarch butterfly (*Danaus plexippus*) may lay eggs and/or on which a monarch butterfly caterpillar will feed and grow, i.e., a milkweed (genus *Asclepias*) plant, such as, for example, but not limited to, common milkweed (*Asclepias syriaca*), swamp milkweed (*Asclepias incarnata*), and tropical milkweed (*Asclepias curassavica*). In other embodiments, the host plant may be rue (*Ruta graveolens*), or parsley (*Petroselinum crispum*), on which swallowtail butterflies, such as, but not limited to, the black swallowtail (*Papilio polyxenes*) or giant swallowtail (*Papilio cresphontes*), may lay eggs and/or on which a swallowtail butterfly caterpillar will feed and grow. In other embodiments of the present inventive concept, the container system may be used for shipment and delivery of a plant, on which live samples, provided separately by the recipient, may be raised. In still other embodiments, the container system may be used for shipment and delivery of live plants, such as potted plants and/or floral arrangements, and the like.

In some embodiments, the live samples may include viable insect eggs provided on the live plant, for example, but not limited to, butterfly eggs. Although not particularly limited by butterfly species, in some embodiments, the butterfly eggs may be monarch butterfly eggs. In other embodiments, the butterfly eggs may be swallowtail butterfly eggs. The plant, including butterfly eggs thereon, may be shipped together in the container of the present inventive concept, and may additionally include further items packaged therewith, such as instructions to rear butterflies and experience observing the lifecycle of butterflies from egg to caterpillar to chrysalis/pupa to adult, and a butterfly net enclosure, as part of a butterfly rearing kit. After rearing, the adult butterflies may be released into the wild in order to benefit, for example, conservation efforts of butterflies such as the monarch butterfly.

The number of eggs that may be included on the plant is not particularly limited. However, in some embodiments, the number of eggs provided on the plant may limited by the size of the plant. For example, a four-foot milkweed plant may only be sufficient to feed about 4 monarch butterfly caterpillars through its lifecycle from egg to chrysalis. As such, a potted plant may be provided with about 2 to about 5 caterpillar eggs thereon.

It will be understood that a plant, on which butterfly eggs may be attached thereto through natural means by a female butterfly, cannot sustain significant amount of abuse, injury, and/or damage during shipping, and recover within the timeframe necessary for maintaining the viability of live samples, such as is required for growing and/or raising caterpillars through their lifecycle from egg to butterfly. Accordingly, containers for shipping live samples should ensure minimal environmental insult and/or damage to a plant with insect eggs attached thereto. Furthermore, it will be appreciated that shipment of a plant including caterpillars/larvae attached thereto, may be disadvantageous in that caterpillars/larvae may become dislodged and fall off the plant due to jostling and/or shaking of the plant during shipment, leading to significant loss of and decreased viability of the live samples during shipment. As such, in some embodiments of the present inventive concept, the live samples are insect eggs, such as butterfly eggs, attached to a host plant, and on which the live samples will proceed through its lifecycle.

Various test shipments have been performed using the container system in accordance with embodiments discussed herein. In conventional shipping systems, such as a simple tray in which a potted plant may be set and shipped in a container, the pot may become dislodged from the tray within the container, and the plant damaged and/or soil spilled out of the pot. The resulting damage to the plant during shipment will have significant impact on the viability of live samples, such as butterfly eggs, attached thereon. In the shipping of a potted plant on which live samples may be attached and/or reared, using the container system of the present inventive concept, the plant arrived in excellent condition with no significant visual damage to the plant or soil spillage. Furthermore, in additional tests, the shipping container of the present inventive concept, with a potted plant contained therein, was subjected to numerous handling abuses, such as shaking, rolling, and tossing the container, which all could potentially occur during shipment, and dropping the container from a height of about 20 feet onto both grass and pavement. Although the box was damaged, the plant suffered no significant damage and no soil leakage was exhibited. The viability of live samples attached to and/or to be reared on the plant is maintained, in spite of the numerous handling abuses that the container was subjected to.

Example embodiments are described above with reference to block diagrams and/or flowchart illustrations of systems and devices. The functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. A die cut tray insert for securing live samples during shipping, the die cut tray insert comprising:
a first face and a second face, the second face opposite and parallel to the first face;
a first assembly and a second assembly each secured at an end to one of the first or second faces and configured to swing between an open position and a closed position such that a pot associated with a live sample is secured on at least two sides when the first and second assemblies are in the closed position, wherein each of the first assembly and the second assembly comprises a hemispherical margin portion on a top surface of the respective assembly and an angled margin portion on an inner side surface of the respective assembly, the angled margin portion configured to conformally surround a portion of a periphery of the pot and secure the pot within the die cut tray insert when the respective assembly is in the closed position; and
a third face and a fourth face, perpendicular to the first and second faces and opposite and parallel to one another, the third face configured to cover a top portion of the pot associated with the live sample and the fourth face configured to contain the pot within the first, second and third faces,
wherein the third face covering the top portion of the pot is configured to reduce spillage from the pot when the first and second assemblies are in the closed position.

2. The die cut tray insert of claim 1, wherein the first and second assemblies are configured to prevent the pot and the live sample positioned therein from at least one of moving or tipping over when the die cut tray insert is positioned in a receptacle for shipping.

3. The die cut tray insert of claim 1, wherein the third face of the die cut tray insert comprises a notch or slot such that a main stalk of the live sample in the pot may slide through the notch or slot when the pot is positioned in the die cut tray insert.

4. The die cut tray insert of claim 1, further comprising a finger hole large enough to stick at least one finger through at a center of an intersection of the first face or the second face and the third face of the die cut tray insert to facilitate slidably removing the die cut tray insert including the live sample in the pot.

5. The die cut tray insert of claim 1, wherein the die cut tray insert comprises a corrugated type fiberboard or paperboard material.

6. A container system for shipment and delivery of live samples, the system comprising:
a receptacle;
a partition set;
a die cut tray insert configured to receive a pot including a live sample, the die cut tray insert including the live sample configured to be surrounded by the partition set and positioned within the receptacle for shipping, wherein the die cut tray insert comprises:
a first face and a second face, opposite and parallel to the first face;
first and second assemblies secured at an end to one of the first or second faces and configured to swing between an open position and a closed position such that the pot associated with the live sample is secured on at least two sides when the first and second assemblies are in the closed position; and
a third face and a fourth face, perpendicular to the first and second faces and opposite and parallel to one another, the third face configured to cover a top portion of the pot associated with the live sample and the fourth face configured to contain the pot among the first, second and third faces, wherein the third face covering the top portion of the pot is configured to reduce spillage from the pot when the first and second assemblies are in the closed position; and a gift box configured to be positioned in the receptacle with the die cut tray insert including the pot and the live sample, wherein the gift box is configured to be positioned on the partition set remote from the die cut tray insert or below the die cut tray insert.

7. A container system for shipment and delivery of live samples, the system comprising:

a receptacle;

a partition set; and a die cut tray insert configured to receive a pot including a live sample, the die cut tray insert including the live sample configured to be surrounded by the partition set and positioned within the receptacle for shipping, wherein the die cut tray insert comprises:

a first face and a second face, the second face opposite and parallel to the first face;

a first assembly and a second assembly each secured at an end to one of the first or second faces and configured to swing between an open position and a closed position such that the pot associated with the live sample is secured on at least two sides when the first and second assemblies are in the closed position, wherein each of the first assembly and the second assembly comprises a hemispherical margin portion on a top surface of the respective assembly and an angled margin portion on an inner side surface of the respective assembly, the angled margin portion configured to conformally surround a portion of a periphery of the pot and secure the pot within the die cut tray insert when the respective assembly is in the closed position; and a third face and a fourth face, perpendicular to the first and second faces and opposite and parallel to one another, the third face configured to cover a top portion of the pot associated with the live sample and the fourth face configured to contain the pot among the first, second and third faces, wherein the third face covering the top portion of the pot is configured to reduce spillage from the pot when the first and second assemblies are in the closed position.

8. The system of claim 7, wherein the system further comprises a gift box configured to be positioned in the receptacle with the die cut tray insert including the pot and the live sample.

9. The system of claim 8, wherein the gift box is positioned on the partition set remote from the die cut tray insert or below the die cut tray insert.

10. The system of claim 8, wherein the receptacle, the partition set, the die cut tray insert, and the gift box comprise a corrugated type fiberboard or paperboard material.

11. The system of claim 6, wherein the receptacle is a box comprising at least one flap configured to be opened and closed to receive the die cut tray insert including the pot and live sample and the partition set positioned thereon.

12. The system of claim 11, wherein the receptacle comprises one or more holes on surfaces thereof to facilitate lifting the container system.

13. The system of claim 6, wherein the partition set comprises four individual partitions configured to combine such that the partition set surrounds leaves and stalks of the live sample in the pot to protect the live sample from damage and environmental elements during shipping.

14. The system of claim 6, wherein the first and second assemblies are configured to prevent the pot and live samples positioned therein from moving at least one of moving or tipping over when the die cut tray insert is positioned in a receptacle for shipping.

15. The system of claim 6, wherein the first assembly and the second assembly each comprise:

a hemispherical margin portion on a top surface the respective assembly; and an angled margin portion on an inner side surface of the respective assembly configured to conformally surround a portion of a periphery of the pot and secure the pot within the die cut tray insert when the respective assembly is in the closed position.

16. The system of claim 6, wherein the third face of the die cut tray insert comprises a notch or slot such that a main stalk of the live sample in the pot may slide through the notch or slot when the pot is positioned in the die cut tray insert.

17. The system of claim 6, further comprising a finger hole large enough to stick at least one finger through at a center of an intersection of the first or second face and the third face of the die cut tray insert to facilitate slidably removing the die cut tray insert including the live samples in the pot.

18. The system of claim 6, wherein the die cut tray is configured to secure a one-gallon trade pot having a depth of 6.25 inches and a diameter of 6.5 inches.

* * * * *

UNITED STATES PATENT AND TRADEMARK OFFICE
CERTIFICATE OF CORRECTION

PATENT NO. : 11,453,544 B2
APPLICATION NO. : 15/930630
DATED : September 27, 2022
INVENTOR(S) : Donna Hughes Pless It is certified that error appears in the above-identified patent and that said Letters Patent is hereby corrected as shown below:

In the Claims

Column 10, Claim 11, Lines 9-10: Please correct "and live sample" to read -- and the live samples --

Column 10, Claim 14, Lines 21-22: Please correct "and live sample" to read -- and the live samples --

Signed and Sealed this
Thirteenth Day of December, 2022

Katherine Kelly Vidal
*Director of the United States Patent and Trademark Office*